United States Patent [19]

Peterson

[11] Patent Number: 4,662,227

[45] Date of Patent: May 5, 1987

[54] APPARATUS FOR MEASURING PULL-OUT RESISTANCE

[75] Inventor: Francis C. Peterson, Woodbury, Conn.

[73] Assignee: Illinois Tool Works Inc., Chicago, Ill.

[21] Appl. No.: 860,709

[22] Filed: May 5, 1986

Related U.S. Application Data

[63] Continuation of Ser. No. 679,843, Dec. 10, 1984, abandoned.

[51] Int. Cl.⁴ .............................................. G01N 3/08
[52] U.S. Cl. ........................................ 73/834; 73/826
[58] Field of Search ................. 73/826, 831, 834, 835, 73/803, 9, 841, 845, 843

[56] References Cited

U.S. PATENT DOCUMENTS

| | | | |
|---|---|---|---|
| 2,780,068 | 2/1957 | Grimes | 73/826 |
| 3,595,072 | 7/1971 | Richards | 73/826 |
| 3,667,288 | 6/1972 | Hargreaves | 73/836 |
| 3,690,160 | 9/1972 | Kriesten | 73/831 |

FOREIGN PATENT DOCUMENTS 2101749  1/1983  United Kingdom ................. 73/826

Primary Examiner—Stewart J. Levy
Assistant Examiner—Robert R. Raevis
Attorney, Agent, or Firm—David I. Roche; Thomas W. Buckman

[57] ABSTRACT

A testing apparatus for measuring the pull-out resistance of fasteners. The apparatus includes a disc rotatably supported by a base. The disc has a bearing surface with a uniform radius. A flexible strap is fixed to the disc so that the strap is carried by the bearing surface as the disc rotates. A torque wrench is used to rotate the disc. The length of the constant radius and the flexible nature of the strap create a constant moment arm, making the torque measured by the wrench directly convertible to pull-out load.

5 Claims, 3 Drawing Figures

U.S. Patent May 5, 1987 4,662,227

APPARATUS FOR MEASURING PULL-OUT RESISTANCE

BACKGROUND AND SUMMARY OF THE INVENTION

This application is a continuation of application Ser. No. 679,843, filed 12/10/84, now abandoned.

The present invention relates to an apparatus for measuring the pull-out resistance of articles embedded in a workpiece. More particularly, the invention relates to a device for making field measurements of fasteners used in the roofing industry.

In roofing, particularly in roof repair, a problem frequently encountered is a wide variation in the strength of the material to which the roof is applied. Varying conditions of disrepair can create widely varying conditions in the field. In order to avoid unnecessarily frequent placement of anchors, it is necessary to get large quantities of test data to evaluate the material into which the anchors are placed. The presence or lack of moisture in roofing material such as gypsum or light weight concrete, can create particularly wide variations in pull-out strength.

Practices in the past have included a rough estimate of pull-out strength by hand removal of sample fasteners. Alternatively, an overly conservative placement has been used.

It is an object of the present invention to provide a portable testing apparatus for testing fasteners in the field.

Another object of the present invention is to provide a testing apparatus which can be used to quickly test fasteners in order to gather large amounts of test data.

Another object of the present invention is to provide a simple, low cost, and durable testing apparatus which can be used by field engineers to determine the placement array of fasteners in a roofing construction.

These and other objects of the present invention are attained with a pull-out testing apparatus comprising a generally flat, at least partially cylindrical disc which is rotatably mounted on a support. The support is comprised of a pair of L-shaped plates which support an axle about which the disc rotates. A flexible spring steel strap is mounted on the disc and extends down to the bottom of the plates. The end of the strap contains a fastener holding block which is adapted to receive the head of a test fastener. Extending rigidly from the disc is a lever arm, which preferably includes a torque wrench which measures torque about the center of the disc. The torque wrench measures torque in inch-pounds, and the radius of the disc is approximately one inch. The torque reading, therefore, is directly convertible to pull-out load associated with the test fastener. Because the spring steel strap is flexible, the line of pull-out is tangent to the disc, which makes the torque reading an accurate measure of pull-out resistance of the test fastener.

DESCRIPTION OF THE PREFERRED EMBODIMENT

Figure 1:
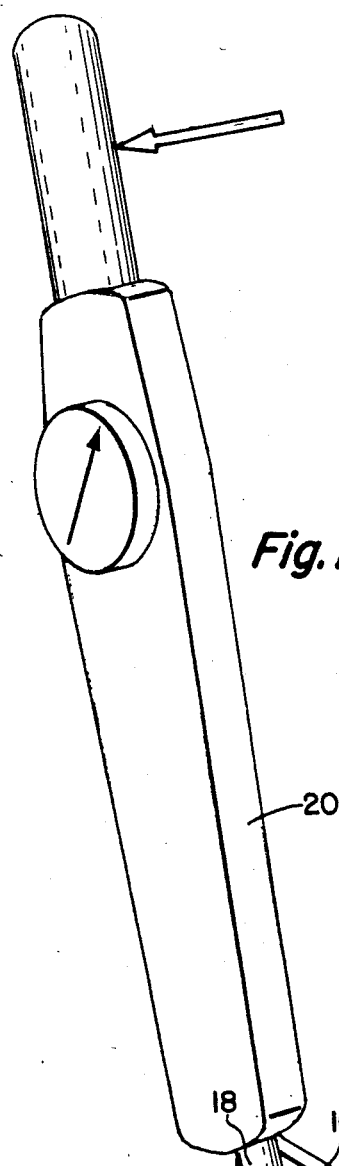
FIG. 1 is a perspective view illustrating the overall configuration of the apparatus of the present invention.

FIG. 1 shows the apparatus 10 comprised of a base 12 which is made up of two plates 14 which support a pulling member or disc 16. Extending from the disc is a lever arm 18 which includes a torque wrench 20. Also attached to the disc and extending in a downward direction is a flexible tension strap 22. The disc 16 is a generally flat cylindrical member with a bearing surface 35 on the periphery of the disc 16. The bearing surface 35 abuts the strap 22 during a test.

The apparatus in FIG. 1 is shown in its position just prior to its engagement with a test fastener 24. The fastener holding block 26 attached to the free end of the strap 22 is adapted to engage the head of the test fastener 24.

It should also be noted that the spacing foot 28 is used to place the head of the fastener a predetermined distance above the workpiece surface 30. The spacing foot 28 includes an open slot 29 which allows the apparatus to be moved laterally out of engagement with the fastener head when the fastener has been installed to a predetermined level.

Figure 2:
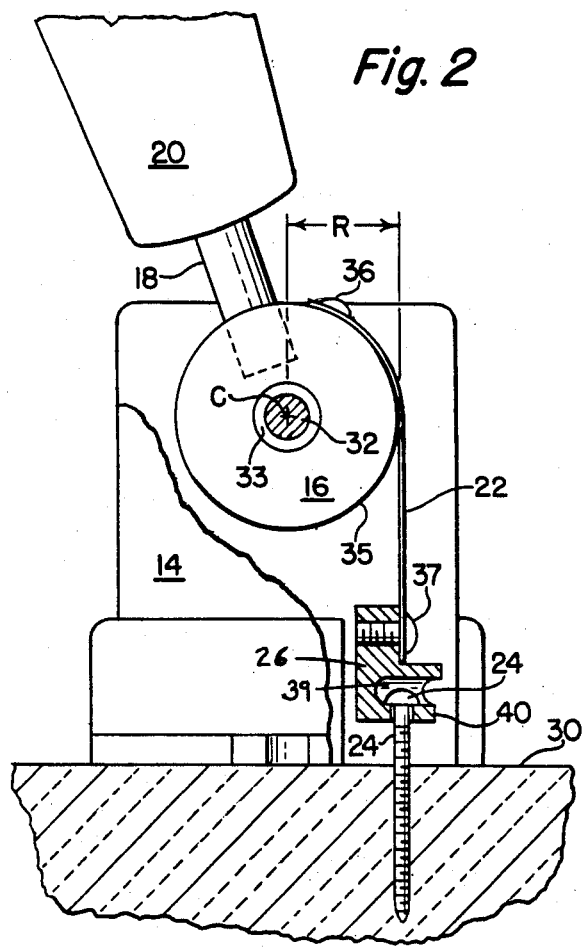
FIG. 2 is a side elevational view in partial section of the apparatus of the present invention.

FIG. 2 shows the apparatus 10 in engagement with the test fastener 24. In this view, it can be seen that the axle 32 supports the bearing 33 around which the disc 16 rotates. The outer periphery of the disc 16 includes a bearing surface 35. The strap 22 is fastened to the disc 16 by a screw 36. The bearing surface 35 is disposed at a constant radius from the axle 32. The flexible strap 22 is adapted to ride on the bearing surface 35 in order to pull the fastener 24 along a line tangent to the bearing surface 35. The radius "R", which corresponds to the distance of the bearing surface 35 from the center of the disc "C", is preferably one inch. By making this distance "R" one inch and by using a torque wrench 20 which measures in inch-pounds, it is possible to make direct conversions from inch-pounds to pounds.

Figure 3:
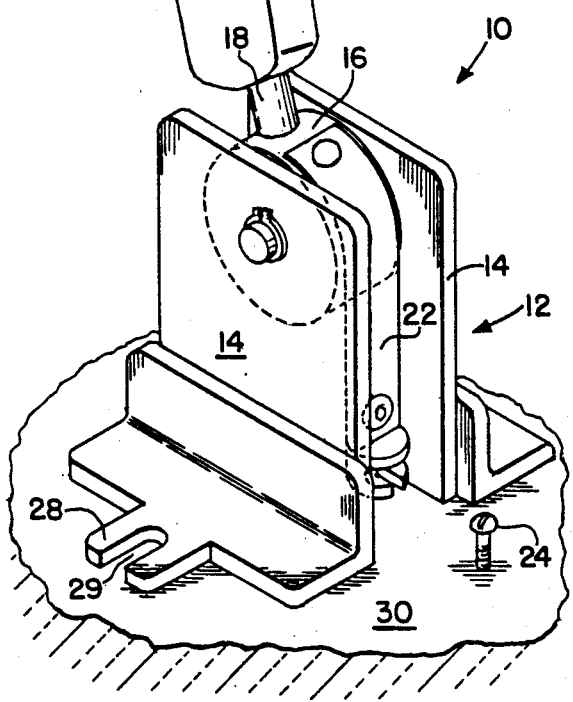
FIG. 3 is a front elevational view in partial section of the apparatus of the present invention.
Figure 3:
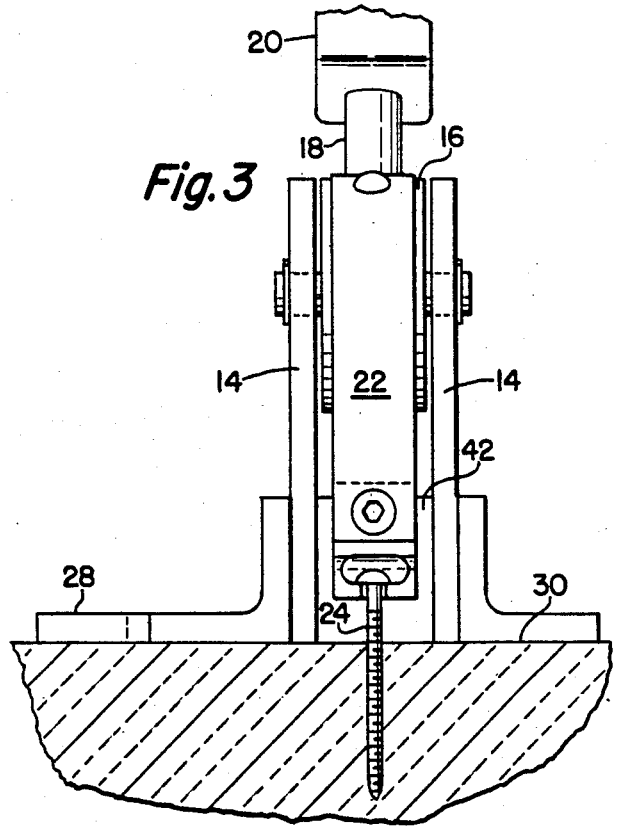

As shown in FIGS. 2 and 3 the holding block 26 is attached to the free end of the strap 22 by a screw 37. The block 26 is comprised of a pair of intersecting slots 39 and 40. The lateral slot 39 extends into the block deep enough to accommodate the full fastener head. The vertical slot 40 extends through the bottom of the block 26. It should be noted that the axis of the fastener should be aligned with the center of the strap 22 in order to avoid eccentricity during the pull-out of the test fastener 24. The slot 40 is deep enough in the horizontal direction to allow such alignment.

A spacing block 42 is used to hold the plates apart. The spacing block 42 is slightly wider than the disc 16 so that the disc 16 freely rotates between the plates 14.

The operation of the apparatus 10 is as follows. A test fastener 24 is placed in the slot 29 in the spacing foot 28 and is driven into the workpiece surface 30. Once the fastener 24 has been installed the holding block 26 which is attached to the free end of the flexible strap 22 is moved into engagement with the fastener head. The axis of the fastener 24 is aligned with the center of the flexible strap when the strap 22 is in a vertical position. As downward force is applied to the torque wrench 20 and the lever arm 18 the disc 16 rotates about its center "C". As the disc 16 rotates, the strap 22 moves upward along the line tangent to the outer periphery of the disc 16 at the bearing surface 35. As continued downward movement of the torque wrench occurs the test fastener 24 is extracted from the workpiece. By choosing the appropriate radial dimension "R" and an appropriately calibrated torque wrench 20, a simple conversion can be used to determine the maximum pull-out offered by the fastener 24.

While the preferred embodiment of the invention has been specifically shown and described, variations, modifications, and alternatives apparent to those skilled in the art are intended to fall within the spirit and scope of the appended claims.

I claim:

1. An apparatus for testing pull-out strength of fasteners comprising: a base, a pulling member carried by said base, said pulling member being rotatable about an axis, an arm extending from said member, said arm including torque measuring means for measuring torque about said axis, a flexible extension of said pulling member, one end of said extension fixed to said pulling member, fastener holding means disposed at an opposite end of said extension for engaging a fastener to be tested, said torque measuring means comprising a torque wrench capable of measuring torque in units of length times units of force, and said pulling member being generally disc-like and having a radius equal to one of said units of length, whereby torque measured by said torque wrench is directly convertible to said units of force of pull-out resistance, said base including a laterally extending slot adjacent extreme lower portions of said base, said slot providing means for preliminarily spacing heads of fasteners away from a workpiece surface from which pull-out strengths of said fasteners are subsequently tested.

2. An apparatus in accordance with claim 1 wherein said pulling member is generally flat and cylindrical, and said flexible extension is a thin strap of spring steel.

3. An apparatus in accordance with claim 1 wherein said holding means is a block adapted to engage a headed fastener, said block having a pair of intersecting slots, a first slot in one end of said block for accommodating a screw shank, a second slot generally perpendicular to and intersecting said first slot for receiving a fastener head.

4. An apparatus in accordance with claim 1 wherein said base includes a pair of plates separated by a spacer, and said pulling member is a generally flat cylindrical disc disposed between said plates and supported about its center by an axle connected to said plates.

5. An apparatus for testing pull-out strength of fasteners comprising: a generally flat cylindrical disc rotatably mounted on a support, said support having means for maintaining said disc in a position perpendicular to a work surface into which a fastener is installed, said support including a pair of disc supporting members disposed on opposite sides of said disc, said disc supporting members having means for resting upon said work surface to maintain said apparatus in a position upright with respect to said work surface, an arm rigidly extending from said disc, said disc having a central axis and a bearing surface disposed at a constant distance from said axis, a flexible tension member attached at one end to said disc, an opposite end of said tension member having connecting means for attaching said tension member to said fastener, torque measuring means for measuring torque about said axis in units of length times units of force, said bearing surface being positioned such that said tension member is held a predetermined constant perpendicular distance from said axis, said perpendicular distance being equal to one of said units of length whereby said torque is directly convertible into pull-out load measured in said units of force.

* * * * *